United States Patent [19]

Vorwerk

[11] Patent Number: 5,235,105
[45] Date of Patent: Aug. 10, 1993

[54] PROCESS FOR THE PRODUCTION OF PURE 3,3',4,4'-TETRAAMINO-BIPHENYL

[75] Inventor: Edgar Vorwerk, Kelkheim, Fed. Rep. of Germany

[73] Assignee: Hoechst Aktiengesellschaft, Frankfurt am Main, Fed. Rep. of Germany

[21] Appl. No.: 910,653

[22] Filed: Jul. 8, 1992

[30] Foreign Application Priority Data

Jul. 12, 1991 [DE] Fed. Rep. of Germany ....... 4123033

[51] Int. Cl.$^5$ .................................. C07C 209/84
[52] U.S. Cl. .................................. 564/309
[58] Field of Search .................................. 564/309

[56] References Cited

U.S. PATENT DOCUMENTS

| 3,390,180 | 6/1968 | Fontana et al. ............... 260/582 |
| 3,943,175 | 3/1976 | Druin et al. ............... 564/309 |
| 4,433,168 | 2/1984 | Schubert et al. ............... 564/309 |

FOREIGN PATENT DOCUMENTS

| 0061168 | 9/1982 | European Pat. Off. . |
| 3111470 | 3/1983 | Fed. Rep. of Germany . |
| 60-158146 | 8/1985 | Japan . |

OTHER PUBLICATIONS

M. Toda et al., Chem. Abs. 104: 1091816 (1986).

Primary Examiner—Richard L. Raymond
Attorney, Agent, or Firm—Connolly and Hutz

[57] ABSTRACT

The present invention relates to a process for the preparation of pure 3,3',4,4'-tetraaminobiphenyl in high yield by ammonolysis of 3,3,-dichlorobenzidine in the presence of copper powder and CuCl. After the crude product has been washed with ammonia water and water, the 3,3',4,4'-tetraaminobiphenyl, thus pretreated, is crystallized in water in the presence of 0 to 5% by weight of activated carbon and of about 1 to 2% by weight of a water-soluble reducing agent at temperatures of about 100° to about 140° C., under a protective gas atmosphere (redissolution). The water-soluble reducing agent is an alkali metal dithionite or alkali metal sulfite. The protective gas used can be nitrogen. The water used in the recrystallization (redissolution water) can be reused in whole or in part in the recrystallization.

13 Claims, No Drawings

PROCESS FOR THE PRODUCTION OF PURE 3,3',4,4'-TETRAAMINO-BIPHENYL

DESCRIPTION

The invention relates to a process for the preparation of pure 3,3',4,4'-tetraaminobiphenyl (abbreviation TAB) in high yield which is carried out with the smallest addition of auxiliaries necessary, if any at all, and with or without recycling of redissolution water, whereby significantly improved yields are obtained of high-quality pure TAB. 3,3',4,4'-Tetraaminobiphenyl is an important starting material for the preparation of, for example, polymers resistant to high temperatures, such as polybenzimidazoles, such as are disclosed, for example, in U.S. Pat. Nos. 2,895,948, 3,174,947, 3,578,644, 4,431,796 and 4,452,967. The preparation of such polymers makes high demands on the TAB used with regard to purity, color and residue content levels. The preparation of 3,3',4,4'-tetraaminobiphenyl is carried out by reaction of 3,3'-dichlorobenzidine with ammonia water in a pressure reactor at 180°-220° C. in the presence of copper catalysts. This exchange reaction of chlorine for amino groups has been described several times, different copper catalysts being used.

According to the process described in U.S. Pat. No. 3,865,876, copper(I) chloride is used as catalyst. In U.S. Pat. No. 3,943,175, the preparation of TAB is described with the use of a catalyst mixture of copper powder and copper(I) chloride. Catalyst mixtures of copper powder and copper(I) chloride (CuCl) are particularly suitable for the reaction and are also used according to the more recent process and preparation descriptions.

Both German Patent 3,111,470 C2 and Japanese Laid-Open Application Sho 60-158,146 disclose preparation processes for TAB using such catalyst mixtures:

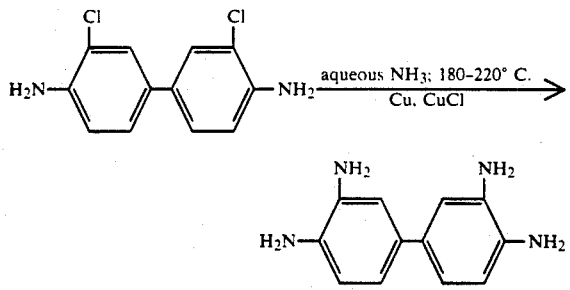

The crude 3,3',4,4'-tetraaminobiphenyl obtained from the reaction, that is after separating off the copper salt-containing ammonia water, is unsuitable for the proposed application and must be subjected to a purification process in order to obtain a TAB which is suitable for processing to give polymers (for example polybenzimidazoles) with regard to color quality, the residual copper content and interfering by-products. For this reason the purification of the crude TAB always received particular attention and all the above-cited patent documents describe detailed purification processes with the aim of preparing material which can be further processed.

The prior art with regard to preparation of pure TAB is described below; in addition, the results and also the specific disadvantages are presented. As already mentioned above a catalyst mixture of copper powder and CuCl has proved suitable in the preparation of 3,3',4,4'-tetraaminobiphenyl from 3,3'-dichlorobenzidine, so that all recent preparation processes (see the cited patent documents) employ said mixture. An essential goal is substantially to remove the added ionic and metallic copper from the TAB, in order to achieve the lowest possible residual copper contents which are also of importance for the good color quality desired. In U.S. Pat. No. 3,943,175 the crude TAB obtained from the reaction is first separated off from the ammoniacal mother liquor and washed with water. Diluted sulfuric acid is used to prepare the acid-insoluble TAB dihydrosulfate, from which free TAB is recovered by reaction with a base. TAB is then recrystallized from water with addition of activated charcoal and diatomaceous earth. For this purpose, approximately a 67-fold quantity of water is employed with addition of 40% activated charcoal and 15% of diatomaceous earth (each relative to the quantity of TAB to be redissolved).

By means of this preparation and purification process, 51.9% of 3,3',4,4'-tetraaminobiphenyl is obtained with a melting point of 175°-181° C. The residual copper content of the material is 0.07% of copper.

German Patent 3,111,470 C2 discloses an improved work-up of crude TAB which has been obtained by reaction of 3,3'-dichlorobenzidine with aqueous ammonia in the presence of a catalyst mixture of copper powder and CuCl. This purification process is also divided into two process steps. The crude TAB is first separated off from the copper-containing ammoniacal reaction mother liquor and then washed with approximately 25% ammonia water and subsequently with water, in order to remove soluble copper compounds from the crude TAB. The water wash serves to remove the residual ammonia. For the ammonia wash, approximately 2-4 parts, relative to the crude TAB, of a roughly 25% ammonia water are used. In the second process step, light TAB with a storage-stable color and only containing copper traces is prepared by recrystallization from water. This recrystallization is carried out under a protective gas atmosphere with addition of activated carbon or diatomaceous earth and a water-soluble reducing agent (sodium dithionite). Relative to the crude TAB, approximately a 29-fold quantity of water is used with addition of approximately 20% of activated carbon and approximately 2% of sodium dithionite. In this manner 71.3% of theory of 3,3',4,4'-tetraaminobiphenyl is obtained with a melting point of 177°-180° C. The residual copper content of the material is approximately 0.005% and the material is slightly sandcolored.

The process of Japanese Laid-Open Application 60-158,146 scarcely provides any advantage over that of German Patent 3,111,470 C2. The Japanese Laid Open Application discloses a purification process for crude TAB which has been obtained by reaction of 3,3'-dichlorobenzidine with aqueous ammonia in the presence of a catalyst mixture of copper powder and CuCl. In a very similar manner to the process of German Patent 3,111,470 C2, the process described in the above-mentioned Japanese-Laid Open Application is divided into two steps: after cooling the reaction mixture, the crude TAB is separated off from the copper-containing ammoniacal reaction mother liquor and is washed with approximately 30% ammonia water and then with water. The ammonia wash serves to separate off soluble copper compounds, whereas residual ammonia is removed by the subsequent water wash. For the ammonia wash, approximately 4 parts, relative to the crude TAB, of approximately 30% ammonia water are used.

In the second process step of the Japanese Laid-Open Application, the crude TAB is purified by means of a recrystallization from water and light, color-stable TAB only containing copper traces is obtained. The recrystallization is carried out under a protective gas atmosphere and also with addition of activated carbon, iron chloride and hydrazine.

Relative to the crude TAB, approximately a 73-fold quantity of water is used; furthermore, approximately 30% of activated carbon, approximately 0.5% of iron chloride and approximately 7% of hydrazine are added. In this manner 75.6% of theory of 3,3',4,4'-tetraaminobiphenyl (relative to dichlorobenzidine) is obtained with a melting point of 177°–178° C. The residual copper content of the TAB is approximately 0.001% (10 ppm) and the material is a whitish earth color.

Although the purification processes, as described above, represent a significant advance in this area, they are not satisfactory in an industrial application. The reaction of 3,3'-dichlorobenzidine with ammonia water in the pressure reactor at 180°–220° C. in the presence of copper powder and copper(I) chloride as catalysts proceeds virtually completely, so that only traces of 3,3'-dichlorobenzidine are present in the reaction mother liquor or in the crude 3,3',4,4'-tetraaminobiphenyl (significantly below 100 ppm; frequently less than 10 ppm).

In a reaction proceeding as well as this, yields of isolated end product of approximately 71–75% cannot be satisfactory, especially if the essential purification stage is a recrystallization, in which these yield losses should not occur. However, the work-up is to be carried out according to high quality requirements made on the end product.

The results described were achieved with previously optimized recrystallization processes in which the quantities of auxiliaries used are accurately specified according to the invention.

According to German Patent 3,111,470 C2, the quantities to be used are:

| | |
|---|---|
| of adsorbent (for example activated carbon) | 10–30% by weight, preferably 15–25% by weight |
| of reducing agent (for example sodium dithionite) | 2–10% by weight, preferably 2–5% by weight. |

All percentages by weight relate to dry, crude TAB, the yield of which, relative to the 3,3'-dichlorobenzidine used, is reported as 93.4% of theory.

According to Japanese Laid-Open Application 60-158,146, the quantities to be used are:

| | |
|---|---|
| of activated carbon | 5–50% by weight, preferably 10–30% by weight |
| of iron chloride | 0–10% by weight, preferably 1–5% by weight |
| of hydrazine | 3–30% by weight, preferably 10–20% by weight. |

All percentages by weight relate here to dry, crude TAB, the yield of which, relative to the 3,3'-dichlorobenzidine used, is reported as 94.1% of theory.

In addition to the unsatisfactory end product yields, the high quantities of waste produced with the use of large quantities of activated carbon are problematic in the processes of the prior art. The use of hydrazine as a reducing agent in the redissolution, with its cancerogenic potential, is, in any case, absurd from today's point of view.

There was therefore a need for a purification process for high-quality TAB, which purification process gives improved yields with the lowest possible amounts of waste.

It has now surprisingly been found that high-quality pure 3,3',4,4'-tetraaminobiphenyl (TAB) can be prepared in high yield from crude TAB which has been prepared in a known manner by ammonolysis of 3,3'-dichlorobenzidine in the presence of copper powder and CuCl and has then been washed with ammonia water and water, by redissolving (recrystallizing) the TAB, thus pretreated, in water in the presence of 0 to about 5% by weight of activated carbon and of about 1 to about 2% by weight of a watersoluble reducing agent, relative in each case to the crude TAB, at temperatures of about 100° C. to about 140° C., preferably of about 105° C. to about 125° C., under a protective gas atmosphere.

Crude TAB, as described in the literature, is prepared for the process according to the invention, for which purpose a catalyst mixture of copper powder and copper(I) chloride is used. After isolating the crude TAB by separating off the reaction mother liquor, the crude material (TAB) is washed in accordance with the literature with ammonia water (concentration 10–35 % of $NH_3$) in order to remove the adhering soluble copper salts, and is then further washed with water, in order to remove adhering residual ammonia.

In this manner, a TAB having a copper content of 0.2–2.0% is obtained, as described in German Patent 3,111,470 C2 or Japanese Laid-Open Application 60-158,146.

The redissolution (recrystallization) according to the invention is carried out without intermediate drying of the pretreated TAB by placing the wet substance under nitrogen into the redissolving vessel.

Relative to the crude, dry TAB (93–94% of theory, relative to 3,3' -dichlorobenzidine), 0–5% by weight, preferably 3 to 4.5% by weight, of activated carbon is added to the redissolution (recrystallization). The addition of activated carbon can alternatively be dispensed with. The activated carbon in the present case acts less as an adsorbent for interfering by-products to be eliminated than as a filter aid for the water-insoluble, unreacted copper powder residues from the catalyst and also insoluble organic material. The addition of activated carbon can be avoided in these respects; however, for processing reasons, more precisely on account of good filtration, an addition of 3 to 4.5% by weight of activated carbon in the redissolution is expedient. In this case, other filtration aids (such as for example silica gel) can alternatively be used in an appropriate quantity and application.

The redissolution is carried out under a protective gas atmosphere, for example a nitrogen atmosphere.

To avoid any oxidative conditions, a water-soluble reducing agent is added to the redissolution. The use of sodium dithionite ($Na_2S_2O_4$) has proved to be expedient; however, other alkali metal dithionites or alkali metal sulfites, such as sodium dithionite or sodium sulfite, or hydrazine can also be used.

Relative to the crude TAB, only about 1 to about 2% by weight of alkali metal dithionite or alkali metal sulfite is used.

The quantity of water required is given by the solubility of TAB at the recrystallization temperature. The redissolution water can be circulated and reused in the next redissolution. Partial recycling of the redissolution water with simultaneous partial purging as waste water is advantageous.

The recrystallization is carried out in the course of 0.5 to 1.5 hours at temperatures of about 110° to about 120° C.

In the process according to the invention, yields of pure TAB of 88.2% of theory, relative to 3,3'-dichlorobenzidine, are obtained. This represents an increase of over 12% compared to the prior art, which denotes an essential advance for an already developed process.

The product qualities obtained are the same as those known from the literature. The pure TAB, prepared by the process according to the invention, is of a whitish to light sand color and has a residual copper content of only 0.001% (10 ppm); sometimes even less. The melting point is 176°-178° C.

These results are achieved with significantly lower additions of auxiliaries than were hitherto conventional, so that the quantities of waste in the process according to the invention are also inevitably significantly reduced.

EXAMPLE 60 kg of 3,3'-dichlorobenzidine, 7.5 kg of CuCl, 2 kg of copper powder and 450 kg of approximately 30% ammonia water, which contains 25 kg of ammonium chloride, are placed in a V2A stainless steel pressure reactor under a nitrogen atmosphere. The reaction mixture is heated for 8 hours at 200°-210° C., a pressure of approximately 65 bar first being established, which falls in the course of reaction to 55-60 bar. After the reaction is completed, the reactor contents are cooled, so that the crude 3,3',4,4'-tetraaminobiphenyl precipitates from the reaction mother liquor and can be separated off at room temperature by means of a filter or a centrifuge under nitrogen. This crude product still contains soluble copper salts which are substantially removed by washing twice with a total of 220 kg of 25% ammonia water. A subsequent water wash with 140 l of water then removes the residual ammonia. These process steps are also carried out under nitrogen. In this manner a crude TAB is obtained, the residual copper content of which is between 0.2 and 2.0%. Unreacted 3,3'-dichlorobenzidine is present only in traces (less than 100 ppm; mostly less than 10 ppm). This crude TAB is not isolated, but is fed directly under nitrogen to the subsequent redissolution.

The crude TAB obtained from the reaction and the subsequent ammonia wash and water wash is placed in 1200 l of water. This quantity contains 600 l of redissolution water recycled from the preceding recrystallization. 2 kg of activated carbon are added, as is 0.6 kg of sodium dithionite ($Na_2S_2O_4$) as water-soluble reducing agent. The redissolution is carried out at 110°-120° C. for 45 minutes under a nitrogen atmosphere. The solution, while still hot, is then passed through a filter, in order to separate off the activated carbon together with insoluble organic material and the copper powder residues of the catalyst. The filter cake is washed with twice 10 l of hot water which is added to the filtrate. The combined filtrates are cooled to room temperature (approximately 25° C.) and the purified TAB precipitating out is filtered off or centrifuged off. After careful drying at 50°-70° C. under a water pump vacuum, 44.8 kg of TAB are obtained, which corresponds to a yield of 88.2% of theory, relative to 3,3'-dichlorobenzidine. The product obtained has a melting point of 176°-178° C. and is of a whitish to light sand color. The residual copper content is 0.001% (10 ppm) or in some cases lower still.

I claim:

1. A process for the preparation of high-quality pure 3,3',4,4'-tetraaminobiphenyl (TAB) in high yield from crude TAB which has been prepared in a known manner by ammonolysis of 3,3'-dichlorobenzidine in the presence of copper powder and CuCl and has then been washed with ammonia water and water, which comprises redissolving the TAB, thus pretreated, in water in the presence of 0 to about 5% by weight of activated carbon and of about 1 to about 2% by weight of a water-soluble reducing agent, relative in each case to the crude TAB, at temperatures of about 100° C. to about 140° C., under a protective gas atmosphere.

2. The process as claimed in claim 1, wherein the redissolution is carried out at temperatures of about 105° to about 125° C.

3. The process as claimed in claim 1, wherein the water-soluble reducing agent used is an alkali metal dithionite or alkali metal sulfite.

4. The process as claimed in claim 1, wherein the reducing agent used is sodium dithionite.

5. The process as claimed in claim 1, wherein the redissolution takes place under nitrogen.

6. The process as claimed in claim 1, wherein the redissolution water used in said redissolving step is taken in whole or in part from a preceding batch of pure 3.3',4,4'tetraaminobiphenyl prepared by said process.

7. The process as claimed in claim 1, including the step of recovering the pure 3,3',4,4'-tetraaminobiphenyl from the solution formed during the redissolving step.

8. The process as claimed in claim 7, wherein the residual copper content in the resulting pure 3,3',4,4'-tetraaminobiphenyl recovered from said solution is 10 parts per million or less.

9. A process for the purification of crude, copper-contaminated 3,3',4,4'-tetraaminobiphenyl, comprising:

obtaining the crude, copper contaminated 3,3',4,4'-tetraaminobiphenyl in the form of an ammonlysis product of 3,3'-dichlorobenzidine which was subjected to ammonolysis in the presence of a copper catalyst and which has been washed to lower the copper content of the crude 3,3',4,4'-tetraaminobiphenyl, thereby providing a washed ammonolysis product which is nevertheless still copper-contaminated, redissolving said washed ammonolysis product in water in the presence of 0to about 5% by weight of activated carbon and of about 1 to 2% by weight of a water-soluble reducing agent, relative in each case to the washed ammonolysis product, at a temperature in the range of about 100° C. to about 140° C., under a protective gas atmosphere, and isolating purified solid 3,3',4,4'-tetraaminobiphenyl.

10. The process as claimed in claim 9, wherein crude, copper-contaminated 3,3',4,4'-tetraaminobiphenyl is prepared by ammonolysis of 3,3'-dichlorobenzidene in the presence of copper powder and CuCl and is washed to lower the copper content of the crude product, and the resulting washed ammonolysis product is subjected to said redissolving step without isolation thereof and while maintaining the protective gas atmosphere.

11. The process as claimed in claim 9, wherein the protective gas atmosphere comprises nitrogen.

12. The process as claimed in claim 9, wherein the washed ammonolysis product has a residual copper content of at least about 0.2%, and the isolated purified solid 3,3',4,4'-tetraaminobiphenyl has a residual copper content of 10 parts per million or less.

13. The process as claimed in claim 9, wherein said redissolving step is carried out in the presence of 0 to 4.5% by weight of activated carbon, relative to the washed ammonolysis product.

* * * * *